United States Patent
Sakamoto

(10) Patent No.: US 11,367,294 B2
(45) Date of Patent: Jun. 21, 2022

(54) IMAGE CAPTURE SYSTEM

(71) Applicant: YAMAHA HATSUDOKI KABUSHIKI KAISHA, Iwata (JP)

(72) Inventor: Masaru Sakamoto, Shizuoka (JP)

(73) Assignee: YAMAHA HATSUDOKI KABUSHIKI KAISHA, Iwata (JP)

(*) Notice: Subject to any disclaimer, the term of this patent is extended or adjusted under 35 U.S.C. 154(b) by 0 days.

(21) Appl. No.: 16/965,237

(22) PCT Filed: Dec. 4, 2018

(86) PCT No.: PCT/JP2018/044628
§ 371 (c)(1),
(2) Date: Jul. 27, 2020

(87) PCT Pub. No.: WO2019/150755
PCT Pub. Date: Aug. 8, 2019

(65) Prior Publication Data
US 2020/0372240 A1 Nov. 26, 2020

(30) Foreign Application Priority Data
Jan. 31, 2018 (JP) .............. JP2018-015169

(51) Int. Cl.
G06V 20/69 (2022.01)
G01N 15/14 (2006.01)
(Continued)

(52) U.S. Cl.
CPC ....... *G06V 20/693* (2022.01); *G01N 15/1475* (2013.01); *G01N 33/4833* (2013.01); *G06V 20/695* (2022.01); *H04N 7/18* (2013.01)

(58) Field of Classification Search
CPC ............. G06K 9/00134; G06K 9/0014; G06K 9/6254; G01N 15/1475; G01N 33/4833;
(Continued)

(56) References Cited

U.S. PATENT DOCUMENTS

2003/0215936 A1* 11/2003 Kallioniemi ............. G01N 1/36
435/40.5
2004/0085443 A1* 5/2004 Kallioniemi ......... G06V 20/693
348/135
(Continued)

FOREIGN PATENT DOCUMENTS

EP 2 457 989 A1 5/2012
JP 2015-223175 A 12/2015
(Continued)

OTHER PUBLICATIONS

The extended European search report issued by the European Patent Office dated Jan. 22, 2021, which corresponds to European Patent Application No. 18903403.6-1210 and is related to U.S. Appl. No. 16/965,237.

(Continued)

Primary Examiner — Jessica M Prince
(74) Attorney, Agent, or Firm — Studebaker & Brackett PC

(57) ABSTRACT

An image capturing system includes a camera unit that captures an image of a cell; a display unit; an input unit that receives input from an operator regarding a selection operation on the cell; an analyzing unit that analyzes the image corresponding to the cell to which the selection operation is given and extracts a feature amount of the cell; and a specifying unit that specifies a recommended cell. The specifying unit sets a parameter that defines a range of the cell to be selected based on the feature amount of the cell to which the selection operation is given up to a first time point. In an image including the cell obtained by image capturing at a second time point later than the first time point, the specifying unit specifies the recommended cell on which the operator is prompted to make a selection based on the parameter.

19 Claims, 9 Drawing Sheets

(51) Int. Cl.
*G01N 33/483* (2006.01)
*H04N 7/18* (2006.01)

(58) Field of Classification Search
CPC ... G01N 2015/1486; G01N 2015/1497; G01N 2015/1006; H04N 7/18; C12M 41/36; C12M 33/06; G06T 2207/20092; G06T 2207/10024; G06T 2207/10056; G06T 2207/20081; G06T 2207/30024; G06T 7/0012
USPC .......................................................... 348/135
See application file for complete search history.

(56) References Cited

U.S. PATENT DOCUMENTS

2008/0315136 A1* 12/2008 Ryu ....................... G02B 21/16
 250/580
2016/0304821 A1 10/2016 Ito
2017/0061618 A1* 3/2017 Matsubara ............... C12Q 1/02
2017/0159002 A1 6/2017 Ito
2018/0189606 A1 7/2018 Tsumura
2019/0017811 A1* 1/2019 Watanabe ................. G06T 7/20

FOREIGN PATENT DOCUMENTS

| JP | 2016-154450 A | 9/2016 |
| WO | 2011/021391 A1 | 2/2011 |
| WO | 2015/087371 A1 | 6/2015 |
| WO | 2016/203956 A1 | 12/2016 |
| WO | 2017/110005 A1 | 6/2017 |

OTHER PUBLICATIONS

International Search Report issued in PCT/JP2018/044628; dated Feb. 26, 2019.

* cited by examiner

FIG.3
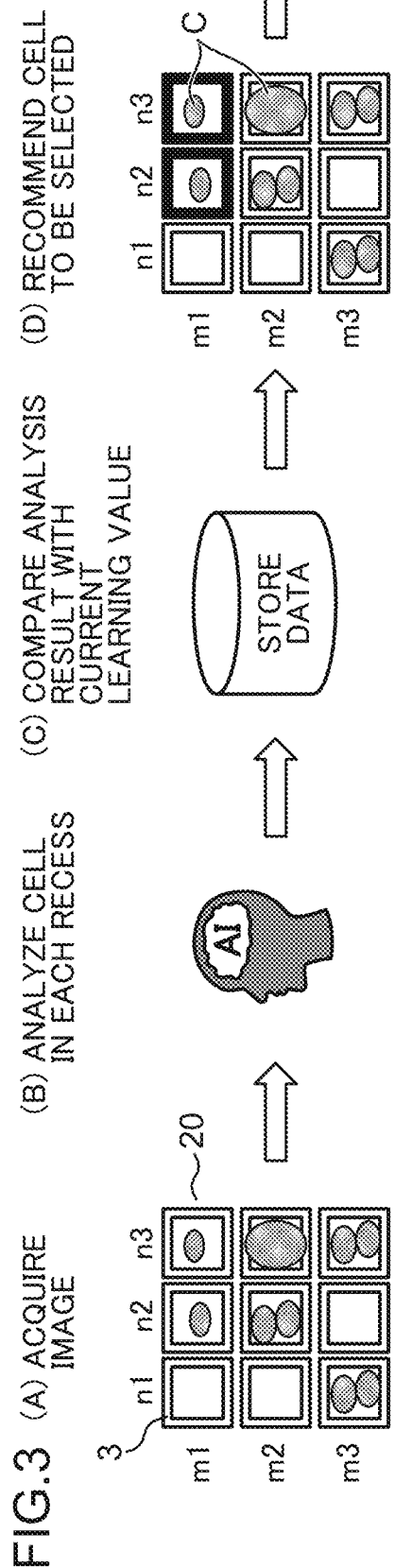
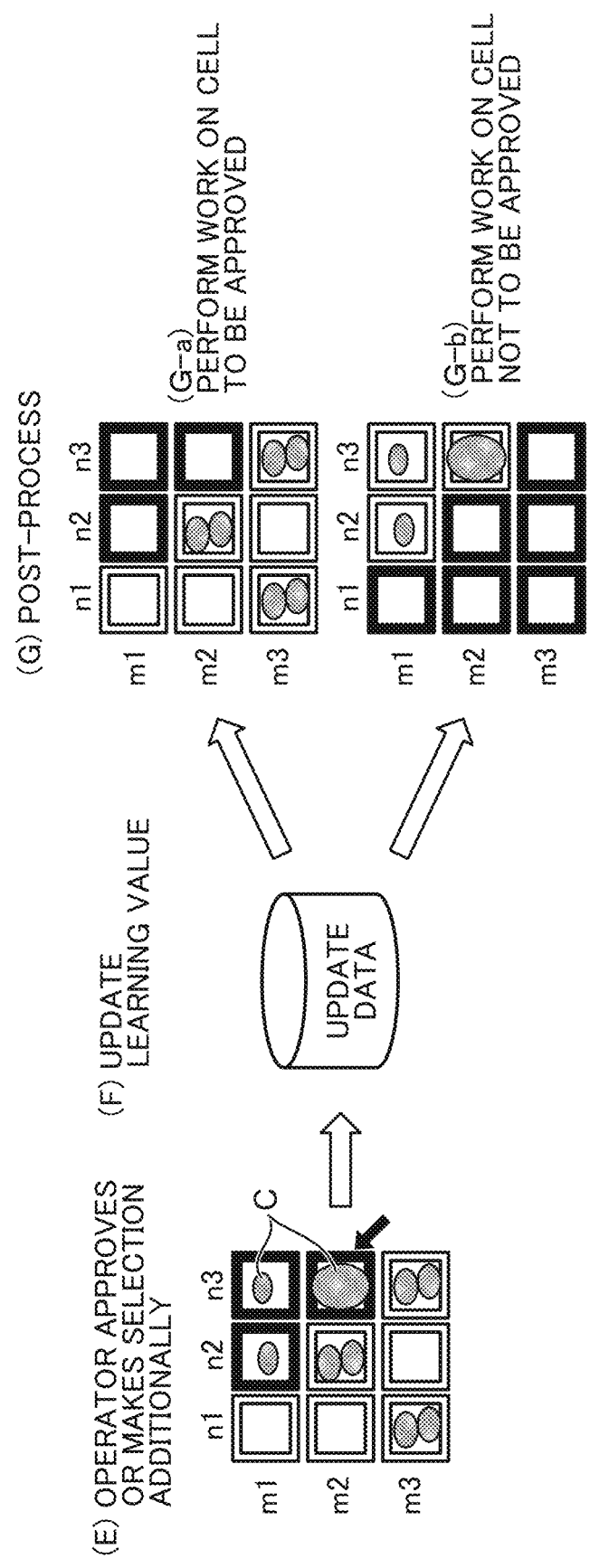

FIG.5
SAMPLE a  SAMPLE b  SAMPLE c
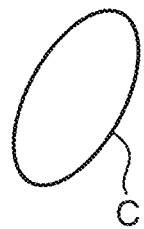 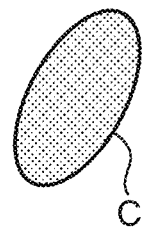 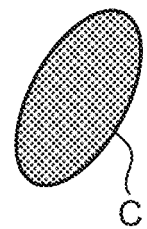
C  C  C

FIG.6
CANCER CELL-1
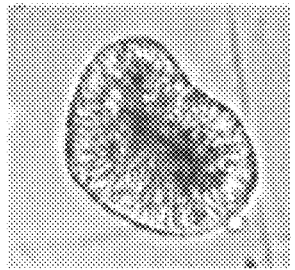
CANCER CELL-2
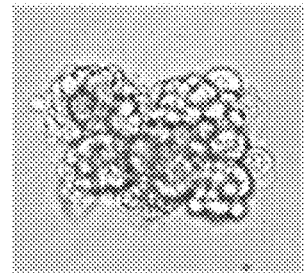
CANCER CELL-3
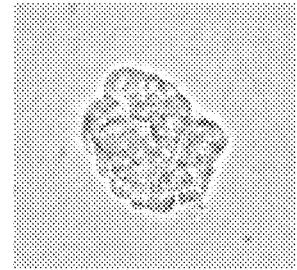

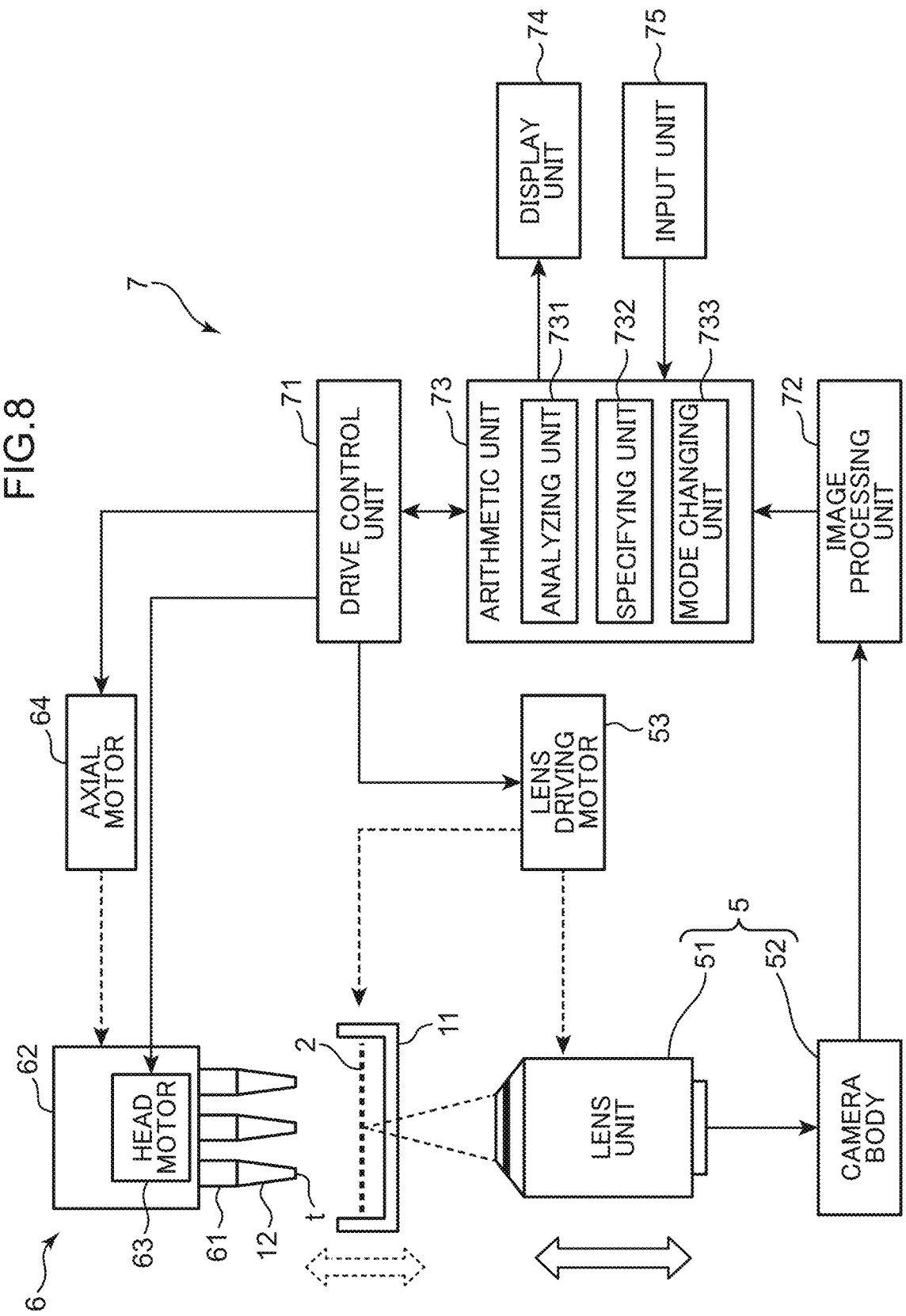

IMAGE CAPTURE SYSTEM

CROSS-REFERENCE TO RELATED APPLICATIONS

This application claims benefit of priority to International Patent Application No. PCT/JP2018/044628, filed Dec. 4, 2018, and to Japanese Patent Application No. 2018-015169, filed Jan. 31, 2018, the entire contents of each are incorporated herein by reference.

BACKGROUND

Technical Field

The present disclosure relates to an image capturing system including an image capturing device that captures an image of a biological subject such as, for example, cells or cell clusters.

Background Art

For example, in medical and biological research applications, image capturing for selecting cells or cell clusters (example of a biological subject; sometimes simply referred to as "cell") may be performed. For example, the work of capturing images of cells scattered on a plate having many accommodating recesses with an image capturing device, selecting desired cells based on the obtained images, and sucking the selected cells with a tip and transferring the cells to a microplate may be performed, as described, for example, in WO 2015/087371 A.

Examples of cell selecting methods include a method of depending on an operator's manual selection and a method of setting in advance a selection reference value about the size, shape, and the like of a cell. The former method is a method of depending on skill of an individual by which the operator observes a captured image of the cell and makes a quality determination based on experience of the operator. The latter method is a method of determining a parameter related to the size and shape of a cell by image processing on the captured image of the cell, and automatically making a quality determination based on whether the parameter satisfies the selection reference value.

The method by the manual selection requires the operator to observe individual cells to make a quality determination, and the work requires a great deal of time. In addition, there is a problem that the quality determination of cells is likely to vary depending on the subjectivity of each individual, the degree of experience, and the like, and it is difficult to obtain uniform quality determination results. In contrast, the method of setting in advance the selection reference value allows automatic determination of quality of cells, reducing the labor. However, there is a problem that it is necessary to consider various parameters in order to prepare an optimum selection reference value in advance, and it is very difficult to set such a selection reference value.

SUMMARY

Accordingly, the present disclosure provides an image capturing system that can accurately select a biological subject and reduce the labor of work for selecting the biological subject.

An image capturing system according to one aspect of the present disclosure includes an image capturing device configured to simultaneously capture an image of a plurality of biological subjects; a display unit configured to display the image including the plurality of biological subjects captured by the image capturing device; an input unit configured to receive input from an operator regarding a selection operation on the plurality of biological subjects displayed on the display unit; an analyzing unit configured to analyze the image corresponding to each of the biological subjects to which the selection operation is given by the input unit and extract a feature amount about the biological subject; and a specifying unit configured to set a parameter that defines a range of each of the biological subjects to be selected based on the feature amount extracted by the analyzing unit for each of the biological subjects to which the selection operation is given up to a first time point or a reference feature amount determined in advance, the specifying unit being configured to configured to specify a recommended biological subject on which the operator is prompted to make a selection based on the parameter in the image including the plurality of biological subjects obtained by image capturing at a second time point later than the first time point.

BRIEF DESCRIPTION OF THE DRAWINGS

FIG. 3 is a diagram schematically showing a flow of cell selecting work using the image capturing system according to the present embodiment;

FIG. 5 is a diagram for describing selection criteria based on a hue of a cell;

FIG. 6 is a diagram for describing selection criteria based on a pattern of a cell;

FIG. 8 is a block diagram of the image capturing system according to the embodiment of the present disclosure.

DETAILED DESCRIPTION

An embodiment of the present disclosure will be described in detail below with reference to the drawings. An image capturing system according to the present disclosure can capture images of a wide variety of biological subjects. In the present disclosure, as the biological subject to be captured, a cell of biological origin can be typically illustrated. Examples of the cell of biological origin here include a single cell (cell) such as a blood cell and single cell, tissue fragment such as Histoculture and CTOS, cell aggregation cluster such as spheroids and organoids, individuals such as zebrafish, nematodes, fertilized eggs, and 2D or 3D colony. In addition, tissues, microorganisms, small species, and the like can be illustrated as the biological subject. The embodiment described below shows an example in which the biological subject is cells or a cell aggregation cluster formed by aggregating several to several hundred thousand cells (hereinafter, collectively referred to simply as "cell C").

[Overall Structure of Cell Transfer Device]

Figure 1:
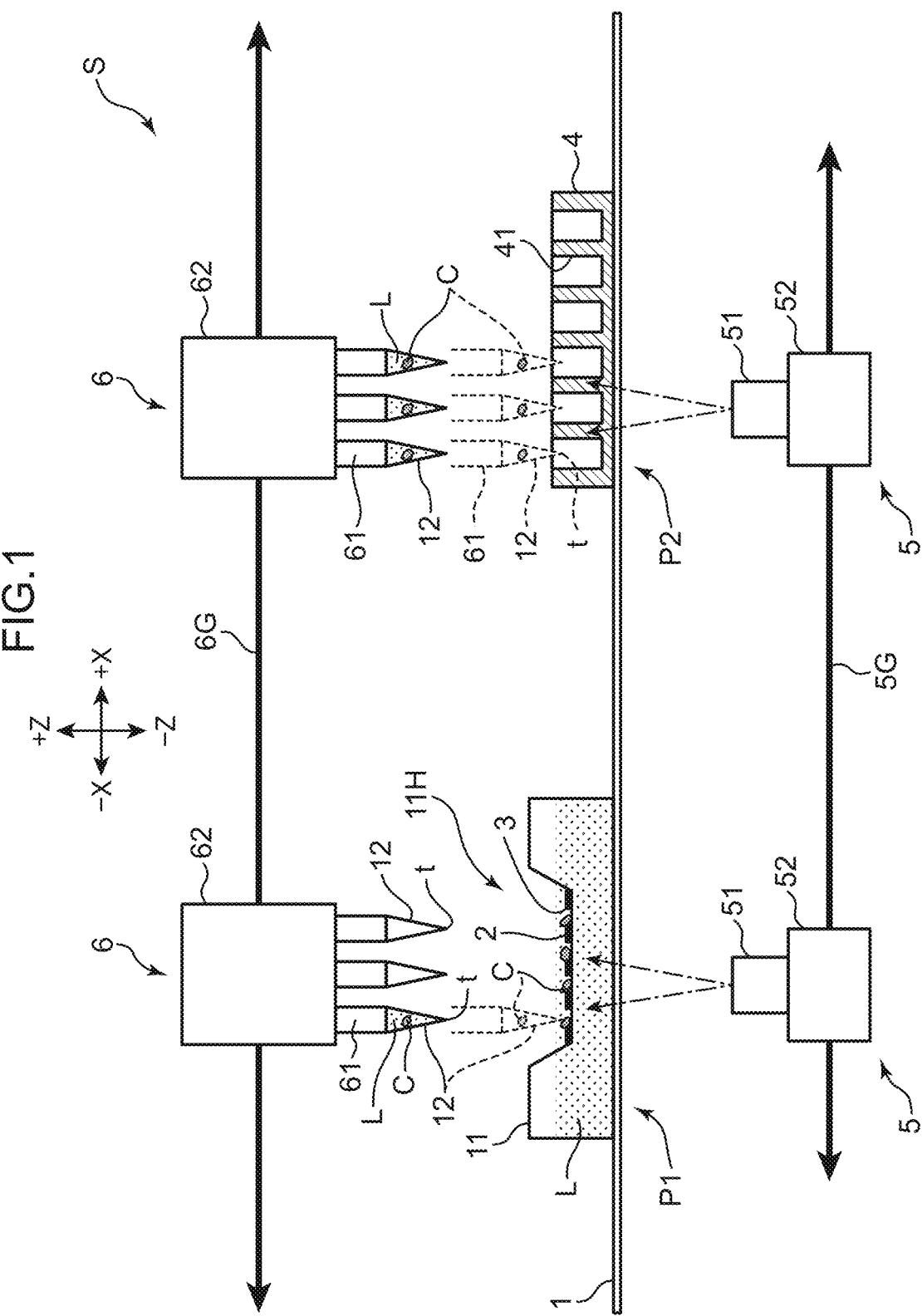
FIG. 1 is a diagram schematically showing a configuration example of a cell transfer device to which an image capturing system according to an embodiment of the present disclosure is applied.

FIG. 1 is a diagram schematically showing an overall configuration of a cell transfer device S to which an image capturing system according to an embodiment of the present disclosure is applied. Here, the cell transfer device S that transfers a cell C between two containers (dish 2 and microplate 4) is illustrated.

The cell transfer device S includes a translucent base 1 having a horizontal mounting surface (upper surface), a camera unit 5 (image capturing device) placed below the base 1, and a head unit 6 placed above the base 1. A selection container 11 including the dish 2 (plate) is mounted at a first mounting position P1 of the base 1, and the microplate 4 is mounted at a second mounting position P2. The head unit 6 includes a plurality of heads 61 to which tips 12 that each suck and discharge the cell C are attached, the heads 61 capable of moving in a Z direction (up-and-down direction). The camera unit 5 and the head unit 6 are movable in the X direction (horizontal direction) and the direction perpendicular to the plane of FIG. 1 (Y direction). The dish 2 and the microplate 4 are mounted on an upper surface of the base 1 within a movable range of the head unit 6.

Roughly, the cell transfer device S is a device in which each of the plurality of tips 12 sucks the cell C individually from the dish 2 of the selection container 11 holding a large number of cells C, and transfers the cell C to the microplate 4, and the plurality of tips 12 simultaneously discharges the cells C to the microplate 4 (well 41). Before the suction of the cells C, the cells C held in the dish 2 are captured by the camera unit 5, and selection work for selecting good quality cells C to be transferred to the microplate 4 is performed.

Each part of the cell transfer device S will be described below. The base 1 is a rectangular flat plate having predetermined rigidity, and part or all of which is formed of a translucent material. The preferred base 1 is a glass plate. The base 1 is formed of a translucent material such as a glass plate, thereby allowing the camera unit 5 placed below the base 1 to capture the selection container 11 (dish 2) and the microplate 4 placed on an upper surface of the base 1 through the base 1.

The selection container 11 is a container that is a transfer source of the cells C, stores a culture medium L, and holds the dish 2 for cell selection in a state of being immersed in the culture medium L. The dish 2 is a plate that holds the cells C, and has a plurality of holding recesses 3 (compartments that accommodate subjects) that can individually accommodate and hold the cells C on an upper surface. The culture medium L is not particularly limited as long as the culture medium L does not deteriorate the properties of the cells C, and can be appropriately selected depending on the type of cell C.

The selection container 11 includes a rectangular upper opening 11H on the upper surface side. The upper opening 11H is an opening for injecting the cells C and picking up the selected cells C. The dish 2 is placed below the upper opening 11H. The selection container 11 and the dish 2 made of a translucent resin material or glass is used. This is to allow the camera unit 5 placed below the selection container 11 to observe the cells C supported in the dish 2.

A plurality of cells C dispersed in a cell culture solution is injected into the selection container 11 from a dispensing tip (not shown). The dispensing tip sucks the cell culture solution together with the cells C from a container that stores the cell culture solution containing the large amount of cells C, and holds the cell culture solution in the dispensing tip. Thereafter, the dispensing tip is moved to an upper air position of the selection container 11 to access the upper surface of the dish 2 through the upper opening 11H. Then, with a tip opening of the dispensing tip immersed in the culture medium L of the selection container 11, the cells C held in the dispensing tip are discharged onto the dish 2 together with the cell culture solution.

The microplate 4 is a container serving as a transfer destination for the cells C, and includes a plurality of wells 41 in which the cells C are discharged. The wells 41 are each a bottomed hole opened on an upper surface of the microplate 4. One well 41 accommodates a required number of (usually one) cells C together with the culture medium L. The microplate 4 made of a translucent resin material or glass is used. This is to allow the camera unit 5 placed below the microplate 4 to observe the cells C supported in the well 41.

The camera unit 5 captures an image of the cells C held in the selection container 11 or the microplate 4 from the lower surface side thereof, and includes a lens unit 51 and a camera body 52. The lens unit 51 is an object lens used in an optical microscope, and includes a lens group that forms a light image with a predetermined magnification and a lens barrel that accommodates the lens group. The camera body 52 includes an image capturing element such as a CCD image sensor. The lens unit 51 forms a light image of an image capturing target on a light receiving surface of the image capturing element. The camera unit 5 is movable in the X and Y directions below the base 1 along a guide rail 5G extending in the left-right direction parallel to the base 1. In addition, the lens unit 51 is movable in the Z direction for a focusing operation.

The head unit 6 is provided for picking up the cells C from the dish 2 and transferring the cells C to the microplate 4, and includes the plurality of heads 61 and a head body 62 to which the heads 61 are assembled. At the tip of each head 61, the tip 12 that sucks (pickup) and discharges the cells C is attached. The head body 62 holds the heads 61 so as to be raised and lowered in the +Z and −Z directions, and is movable in the +X and −X directions along a guide rail 6G. Note that the head body 62 is also movable in the Y direction.

[Details of Dish]

Figure 2A:
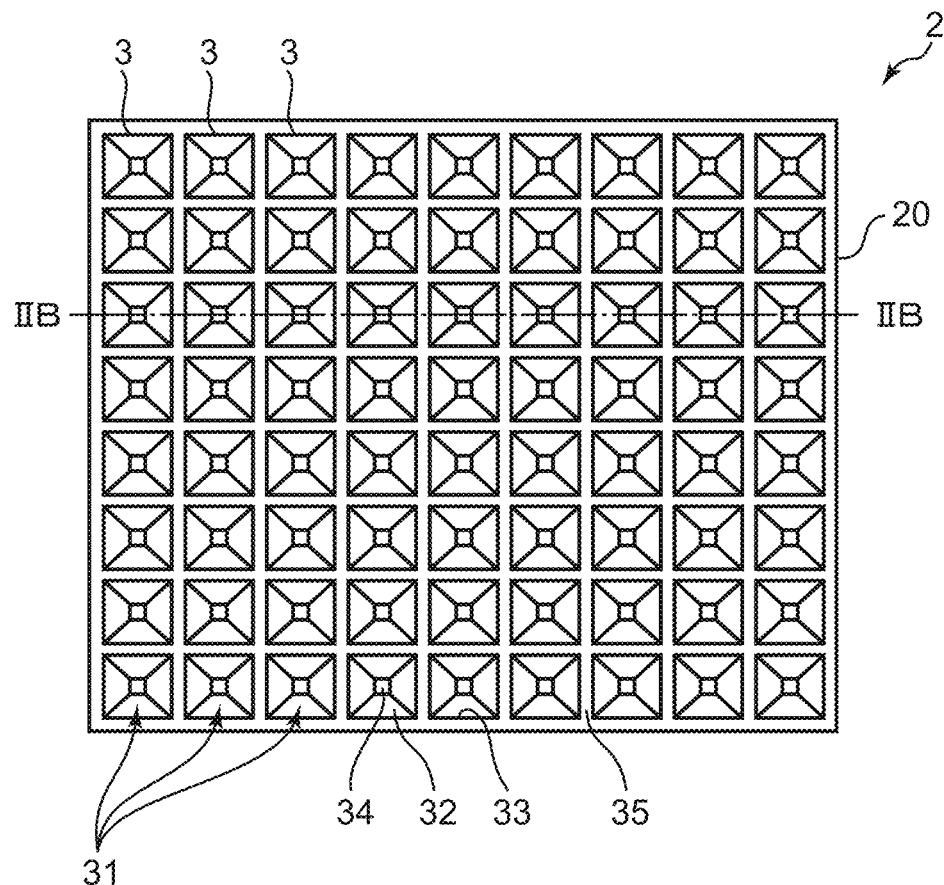
FIG. 2A is a top view of a dish included in a selection container used in the cell transfer device.
Figure 2B:
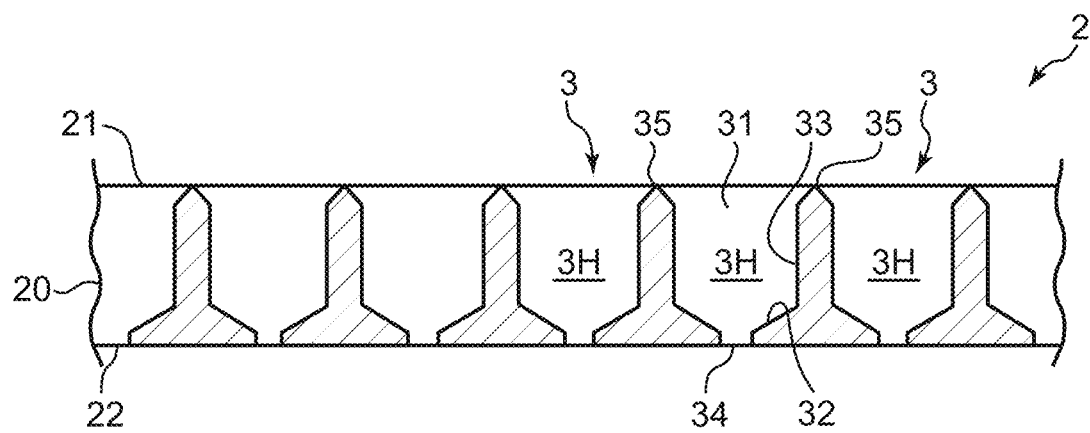
FIG. 2B is a cross-sectional view taken along line IIB-IIB of FIG. 2A.

Detailed structure of the dish 2 will be described. FIG. 2A is a top view of the dish 2, and FIG. 2B is a cross-sectional view taken along line IIB-IIB of FIG. 2A. The dish 2 includes a dish body 20 and a plurality of holding recesses 3 formed in the dish body 20. The dish body 20 includes a flat plate-shaped member having a predetermined thickness and includes an upper surface 21 and a lower surface 22. Each holding recess 3 includes a cell C receiving opening (opening portion 31) on the upper surface 21 side. The dish 2 is immersed in the culture medium L in the selection container 11. In detail, the dish 2 is held in the selection container 11 with a space between the lower surface 22 and a bottom plate of the selection container 11 while the upper surface 21 of the dish body 20 is immersed in the culture medium L in the selection container 11 (see FIG. 1).

Each of the holding recesses 3 includes an opening portion 31, a bottom portion 32, a cylindrical wall surface 33, a hole portion 34, and a boundary portion 35. The present embodiment shows an example in which the holding recesses 3 that are square in top view are arranged in a matrix. As shown in FIG. 2B, the plurality of holding recesses 3 is arranged in a matrix at a predetermined recess arrangement pitch.

The opening portion 31 is a square opening provided on the upper surface 21, and has a size that allows entrance of a tip opening portion t of the tip 12 for selection. The bottom portion 32 is positioned inside the dish body 20 and near the lower surface 22. The bottom portion 32 is an inclined surface that gently inclines downward toward the center (center of the square). The cylindrical wall surface 33 is a wall surface extending vertically downward from the opening portion 31 toward the bottom portion 32. The hole portion 34 is a through hole vertically penetrating between the center of the bottom portion 32 and the lower surface 22. The boundary portion 35 is a portion that is positioned on the upper surface 21 and serves as an opening edge of each holding recess 3, and is a ridge line that partitions the holding recesses 3 from each other.

The bottom portion 32 and the cylindrical wall surface 33 of each holding recess 3 define an accommodation space 3H that accommodates the cell C. It is generally intended that one cell C is accommodated in the accommodation space 3H. The hole portion 34 is provided to allow a small cell or impurities having a size other than a desired size to escape from the accommodation space 3H. Therefore, the size of the hole portion 34 is selected such that the cell C having the desired size cannot pass through but a small cell and impurities other than the desired size can pass through. Accordingly, the cell C to be selected is trapped in the holding recess 3, while impurities and the like fall from the hole portion 34 to the bottom plate of the selection container 11.

[Flow of Cell Selecting Work]

Subsequently, an overall flow of the selecting work of the cells C using the image capturing system of the present embodiment will be described. FIG. 3 is a diagram schematically showing procedures (A) to (G) of the cell selecting work using the image capturing system according to the present embodiment. In the first procedure (A), the camera unit 5 captures an image of the dish 2 to acquire an image of the cells C supported in the dish 2. The lens unit 51 of the camera unit 5 has an angle of view that can simultaneously capture an image of a plurality of cells C (biological subjects). That is, the lens unit 51 has an angle of view that can capture the plurality of holding recesses 3 of the dish 2 shown in FIG. 2 by one image capturing operation.

The procedure (A) shows an example in which an image of the holding recesses 3 of a 3×3 (m1 to m3×n1 to n3) matrix is captured by one image capturing operation. The example here shows a state in which one relatively small cell C is held in each of the holding recesses 3 of m1n2 and m1n3, one relatively large cell C is held in the holding recess 3 of m2n3, two cells C are held in each of the holding recesses 3 of m2n2, m3n1, and m3n3, and no cell C is held in other holding recesses 3.

In the subsequent procedure (B), a feature amount of the cell C held in each holding recess 3 is extracted by analyzing the image acquired in the procedure (A). As will be described later, examples of the feature amount include an amount of cell C obtained from the number, area, estimated volume, and the like of the cell C, color and pattern of the cell C, and light intensity when the cell C is fluorescent. Analysis results of the cell C in each holding recess 3 are digitized.

In the next procedure (C), the analysis results obtained in the procedure (B) are compared with a parameter defining the range of the cell C to be selected. The parameter is a parameter indicating the range of the feature amount of the cell C that is preferable as a selection target. The parameter is obtained from past analysis results of the cell C based on images obtained by image capturing until this time and selection results (selection operation up to a first time point). The parameter is, so to speak, a learning value of the selection criterion in the current situation. Note that in a case of initial selection processing or the like, if the learning value of the selection criterion does not yet exist, a parameter set based on a reference feature amount determined in advance as the cell C preferable for selection is compared with the analysis result obtained in the procedure (B).

In the subsequent procedure (D), a recommended cell C (recommended biological subject) on which the operator is prompted to make a selection as a transfer target is specified based on the comparison result of the procedure (C). The recommended cell C is specified depending on whether the feature amount of each cell C contained in the image obtained by the image capturing this time (image capturing at a second time point later than the first time point) belongs to the range of the parameter. Then, the recommended cell C is displayed to the operator on a display unit such as a monitor. The illustrated procedure (D) shows an example in which the cells C supported in the holding recesses 3 of m1n2 and m1n3 (recommended cells C) are recommended to the operator. A display for causing the operator to recognize that selection is prompted is added to the recommended cell C (enclosing the cell C with a high-luminance marker, adding a symbol or the like as a mark, or the like).

Subsequently, in the procedure (E), approval work of the recommended cell C is performed by a manual operation of the operator. This approval work is work for the operator to determine whether the recommended cell C presented from the image capturing system side in the procedure (D) may be actually treated as the cell C to be selected as the transfer target in light of the operator's own experience. Here, the cells C of m1n2 and m1n3 correspond to the recommended cell C. When the operator determines that these cells C are the cell to be selected for transfer, the operator performs an approval operation. When the operator determines that these cells C are not to be selected, the operator performs a disapproval operation.

Also, in the procedure (E), it is determined whether a cell C that should be treated as the selected cell C exists among the cells C that are not treated as the recommended cell C in the procedure (D) by the image capturing system side. Specifically, the operator determines whether there is a cell C to be transferred among the cells of m2n2, m2n3, m3n1, and m3n3 that are not the recommended cell C. When such a cell C exists, the operator additionally performs the operation of selecting the cell C. The illustrated procedure (E) shows an example in which the recommended cells C of m1n2 and m1n3 are approved, and the cell C of m2n3 is additionally selected (additionally approved).

In the subsequent procedure (F), the parameter (learning value) that defines the range of the cell C to be selected is updated based on the operator's approval and a result of the additional selection. In the procedure (E), the recommended cell C presented is approved, but the cell C of m2n3 is additionally selected. That is, the recommended cell C presented by the image capturing system does not agree with the cell C actually selected by the operator. In this case, with reference to the analysis result (feature amount) derived in the procedure (B) on the actually selected cell C, the parameter (learning value) is corrected such that those cells C fall within a category of "cell to be selected". Then, when operations of the procedures (A) to (E) are performed again on each cell C included in the image obtained by the next image capturing (image capturing at a third time point later than the second time point), the recommended cell C is specified based on the corrected parameter.

In the post-process of the procedure (G) to be executed after the procedure (F), predetermined work is performed on the cell C approved and additionally approved by the operator (procedure (G-a)). Alternatively, predetermined work is performed on the cell C that has not been approved (procedure (G-b)). A typical example of the predetermined work is pickup and transfer of the cell C. In the procedure (G-a), the cells C of m1n2, m1n3, and m2n3 (cells C to which the selection operation is given) are picked up. Meanwhile, when the procedure (G-b) is performed, the work for picking up the cells C existing in the holding recesses 3 other than m1n2, m1n3, and m2n3, or the additional work on the cell C is performed.

[Example of Extracting Feature Amount of Cell]

Subsequently, a specific example of extracting the feature amount of a cell C from an image will be described. In the present embodiment, an image of cells is captured in a state where the cells are accommodated in the holding recesses 3 of the dish 2 (compartments of the plate), the image obtained by the image capturing is analyzed, and the feature amount of the cell C is extracted in units of individual holding recess 3. Such a feature amount that easily appears in the image is the shape of the cell C or the amount of the cell C accommodated in one holding recess 3.

Figure 4A:
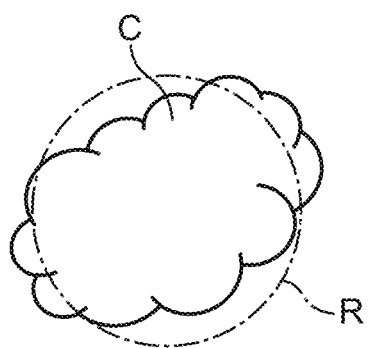
FIG. 4A is a diagram showing one example of a shape of a cell.

The shape of the cell C can be evaluated by roundness of the cell C as shown in FIG. 4A, for example That is, the shape of the cell C can be evaluated by digitizing to what extent the shape of the outer contour of the cell C specified from a two-dimensional image is close to the perfect circle R. The amount of cell C can be evaluated from, for example, the number of cells C accommodated in one holding recess 3, the area of the cell C on the two-dimensional image, estimated volume of the cell C estimated from the contour of the cell C on the two-dimensional image, and the like.

Figure 4B:
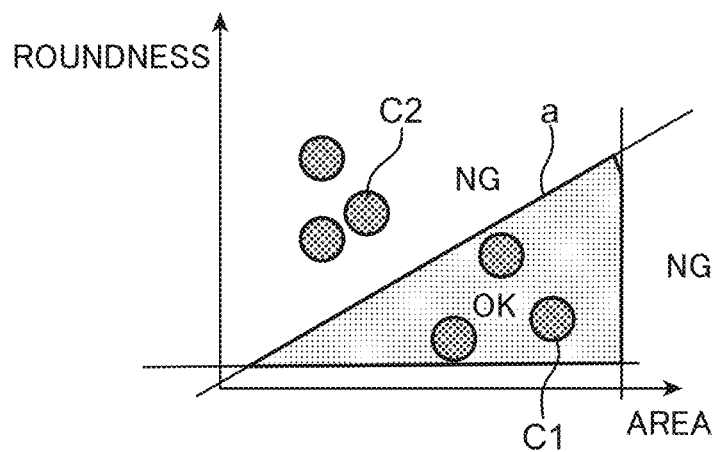
FIG. 4B is a graph for describing one example of selection criteria based on the shape of a cell.

FIG. 4B shows an example in which the shape (roundness) of the cell C and the area of the cell C are extracted as the feature amount, and the recommended cell C is specified from combination of the shape and the area of the cell C. The roundness of the cell C often affects the soundness of the cell C. The area of the cell C is an indicator that directly indicates the size of the cell C. Therefore, the recommended cell C can be specified by performing the process of recommending (OK) the cell C1 whose roundness and area are within a certain range (triangular region indicated by symbol a in the figure; this is determined by the learning value), and not recommending (NG) the cell C2 outside the region a.

The number of cells C is an indicator that is OK when one cell C is accommodated in one holding recess 3 and is NG when a plurality of cells C is accommodated. If a plurality of cells C are accommodated in one holding recess 3, the cells C will be observed in a two-dimensional image in which the cells C are superimposed, making it difficult to perform evaluation itself of each individual cell C. That is, it can be said that the number of cells C is an indicator of whether to avoid extraction of the feature amount because an accurate analysis result cannot be obtained, rather than the property of the cells C themselves.

The estimated volume of the cell C is also an indicator indicating the size of the cell C. The estimated volume may be obtained, for example, by estimating the three-dimensional shape of the cell C from the contour of the cell C shown in one two-dimensional image. The estimated volume may be obtained by estimating the three-dimensional shape of each contour of the cell C that appears in a plurality of two-dimensional images obtained by changing the focal position for the cell C in the Z direction.

The feature amount of the cell C can be a feature amount based on the color of the cell C. The hue of the cell C often reflects the health or life and death of the cell C. FIG. 5 is a diagram for describing selection criteria based on the hue of the cell C. For example, assuming that there are samples a, b, and c of cells C with different hues, the cell C may be evaluated by the hue, such as the sample a is a healthy cell C, the sample b is a living but unhealthy cell C, and the sample c is a dead cell C. In this case, it is possible to specify the recommended cell C by extracting, for example, average luminance of the cells C as the feature amount from the captured image and using the appropriate average luminance between the samples a and b (which is determined by the learning value) as a selection threshold.

The feature amount of the cell C can be a feature amount based on the pattern of the cell C. The pattern of the cell C that appears on the captured image may represent the type of cell C. FIG. 6 shows photographs of different types of cancer cell-1, cancer cell-2, and cancer cell-3. The cancer cell-1 indicates a colon cancer, the cancer cell-2 indicates an endometrial cancer, and the cancer cell-3 indicates a lung cancer. In this way, the pattern of the cell C observed on an image differs depending on the type of cancer cell. Therefore, by linearizing and quantifying the pattern, the pattern can be digitized as the feature amount. Then, the recommended cell C can be specified by setting an appropriate parameter (this is determined by the learning value) that distinguishes the feature amount based on the pattern of the cell C to be selected from the feature amount based on the pattern of another cell C.

Figure 7A:
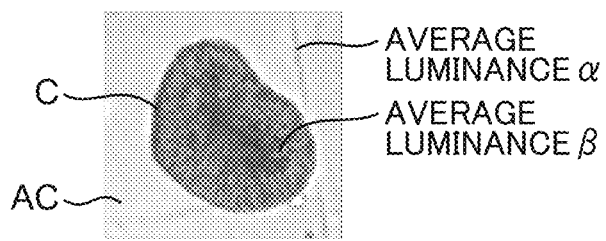
FIGS. 7A and 7B are diagrams for describing selection criteria based on light intensity of a cell.
Figure 7B:
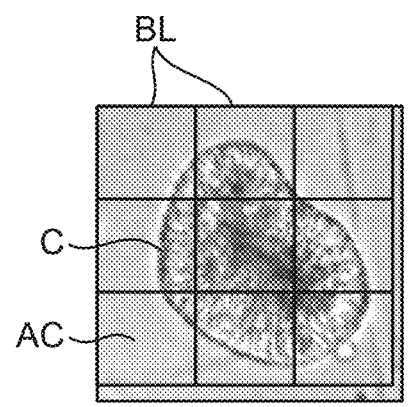

Furthermore, the feature amount of the cell C can be a feature amount based on light intensity of the region of the cell C on the image. The intensity of light emitted by the cell C, particularly the intensity of light emitted by the cell C when the cell C becomes fluorescent by reacting with an appropriate reagent, may be a criterion for evaluating the soundness of the cell C. Therefore, as illustrated in FIG. 7A, the difference between the average luminance $\alpha$ (light intensity) of the peripheral region AC (generally culture medium) of the cell C on the image and the average luminance $\beta$ of the cell C can be used as a digitized feature amount. Then, the recommended cell C can be specified by using appropriate average luminance between the average luminance $\alpha$ and the average luminance $\beta$ (which is determined by the learning value) as the selection threshold. Note that as shown in FIG. 7B, it can be determined whether the cell C satisfying predetermined average luminance exists in the image by dividing the cell C and the peripheral region AC thereof into a plurality of blocks BL on the image, calculating the average luminance in each block BL, and confirming that a place exists where the average luminance varies significantly.

[Configuration of Image Capturing System]

FIG. 8 is a block diagram of the image capturing system according to the embodiment of the present disclosure. The image capturing system includes the camera unit 5 that captures the image capturing target on an image capturing optical axis, a control unit 7 that controls an operation of the lens unit 51 and performs predetermined processing based on image information acquired by the camera body 52, a lens driving motor 53 that moves the lens unit 51 up and down, a display unit 74, and an input unit 75. FIG. 8 shows the dish 2 accommodated in the selection container 11 as the image capturing target. Note that the control unit 7 also controls the pickup operation and transfer operation of the cell C by controlling a head motor 63 in the head unit 6 and an axial motor 64.

The lens driving motor 53 rotates forward or backward to move the lens unit 51 in an up-and-down direction with a predetermined resolution via a power transmission mechanism (not shown). By this movement, the focus position of the lens unit 51 is adjusted to the cells C supported in the dish 2. Note that as shown by the dotted line in FIG. 8, the selection container 11 itself or the stage on which the selection container 11 is mounted (base 1) may be moved up and down, not by the lens unit 51 but by another motor that substitutes the lens driving motor 53.

The head motor 63 is a motor that serves as a drive source for the ascent and descent operation of the heads 61 with respect to the head body 62, and for the operation of generating suction force and discharge force at the tip opening portion t of the tips 12 attached to the head 61. The axial motor 64 is a motor that serves as a drive source for moving the head unit 6 (head body 62) along the guide rail 6G (FIG. 1).

The control unit 7 includes, for example, a personal computer or the like, and operates to functionally include a drive control unit 71, an image processing unit 72, and an arithmetic unit 73 by executing a predetermined program.

The drive control unit 71 controls operations of the lens driving motor 53, the head motor 63, and the axial motor 64. Specifically, the drive control unit 71 gives control pulses for moving the lens unit 51 in an up-and-down direction at a predetermined pitch (for example, tens of μm pitch) to the lens driving motor 53 for the focusing operation. Also, although not shown in FIG. 8, the drive control unit 71 also controls an operation of a camera axis drive motor that moves the camera unit 5 along the guide rail 5G. Furthermore, the drive control unit 71 also controls mechanical operations of the head unit 6. The drive control unit 71 controls the head motor 63 to control the raising and lowering operation of the heads 61 and the operation of generating suction force or discharge force at the tip opening portion t of the tips 12.

The image processing unit 72 performs image processing such as edge detection processing and pattern recognition processing with feature amount extraction on image data acquired by the camera body 52. The image processing unit 72 acquires the image data of the dish 2 supporting the cells C and recognizes the cells C existing on the dish 2 (holding recesses 3) by the image processing.

The arithmetic unit 73 mainly performs various analyses on the cell C on the image specified by the image processing unit 72, and also performs processing of specifying the recommended cell C to be presented to the operator. The arithmetic unit 73 functionally includes an analyzing unit 731, a specifying unit 732, and a mode changing unit 733.

The analyzing unit 731 performs processing of extracting the feature amount of the cell C by analyzing the image of the cell C. The feature amount to be extracted includes the shape, number, area, estimated volume, color, pattern, light intensity, or the like of the cell C as described above with reference to FIGS. 4 to 7. The analyzing unit 731 digitizes these feature amounts.

As described above with reference to FIG. 3, the specifying unit 732 performs processing of specifying the recommended cell C to be presented to the operator by comparing the parameter derived based on the operator's past cell selection record with the feature amount extracted by the analyzing unit 731 about the cell C included in the image acquired by the image capturing this time. The specifying unit 732 sets the parameter that defines the range of the cell C to be selected based on the feature amount extracted by the analyzing unit 731 about the cell C selected by the operator up to the specified first time point. This parameter is the learning value of the cell C selection criterion at the first time point. Then, in the image including the cell C obtained by the image capturing at the second time point later than the first time point, the specifying unit 732 specifies the recommended cell C on which the operator is prompted to make a selection based on the parameter. That is, among the cells C included in the image acquired at the second time point, the cell C having the feature amount belonging to the range of the parameter is specified as the recommended cell C.

Furthermore, as described in the procedures (E) and (F) of FIG. 3, in the selection operation of the cell C in the image obtained by the image capturing at the second time point, when a cell C that does not agree with the recommended cell C specified earlier is selected, the specifying unit 732 corrects the parameter based on the feature amount of the selected cell C. That is, the learning value of the selection criterion of the cell C at the first time point is updated. Then, in the image of the cell C obtained by image capturing at the third time point later than the second time point, the specifying unit 732 performs processing of specifying the recommended cell C based on the updated parameter.

The mode changing unit 733 performs processing of changing an operation mode between a manual operation mode of receiving an approval operation of the operator about the recommended cell C and an automatic approval mode of automatically approving the recommended cell C. In other words, the manual operation mode is to sequentially update the parameter (learning value) according to the selection result of the operator as described above. Meanwhile, without performing such update and without receiving the selection operation from the operator, the automatic approval mode treats the recommended cell C specified by the specifying unit 732 as the cell C for which the selection operation is received. It is assumed that, as the learning of the parameter progresses, the accuracy of specifying the recommended cell C increases to such an extent that intervention of the operator's selection operation is no longer required. At such timing, the mode changing unit 733 changes the operation mode from the manual operation mode to the automatic approval mode. This makes it possible to completely automate the cell C selection work.

The display unit 74 is a display that displays images captured by the camera unit 5. In the present embodiment, the display unit 74 displays the image of the dish 2 captured by the camera unit 5, that is, the image including the plurality of cells C supported in the plurality of holding recesses 3. In addition, a predetermined display that can be easily identified by the operator is added to the recommended cell C.

The input unit 75 includes a keyboard, a mouse, or the like, and receives input from the operator regarding the selection (approval) operation for the cell C displayed on the display unit 74. The operator's approval operation and additional approval operation described in the procedure (E) of FIG. 3 are received by the input unit 75.

[Flow of Cell Selecting Operation]

Figure 9:
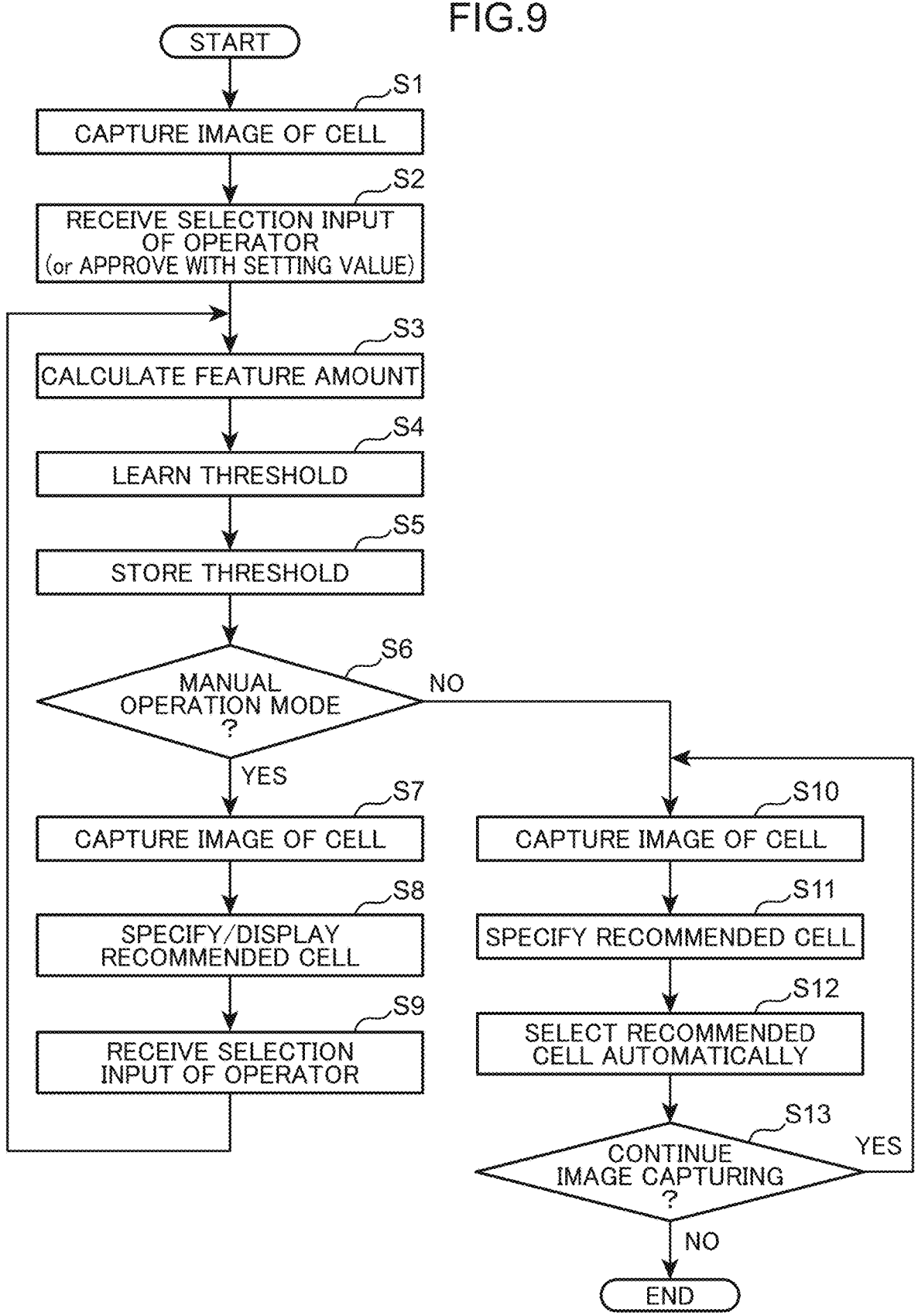
FIG. 9 is a flowchart of a cell selecting operation using the image capturing system.

Subsequently, the cell selecting operation using the image capturing system of the present embodiment shown in FIG. 8 will be described with reference to the flowchart shown in FIG. 9. When the process starts, the camera unit 5 captures an image of the dish 2. A cell suspension has been dispensed in the dish 2 in advance. The camera unit 5 captures an image of the cells C accommodated in the holding recesses 3 of the dish 2 (step S1/image capturing at the first time point). At this time, the drive control unit 71 drives the lens unit 51 to perform the focusing operation on the cells C on the dish 2. The captured image is displayed on the display unit 74 as shown in the procedure (A) in FIG. 3, for example.

Next, the input unit 75 receives input of the first selection operation from the operator regarding which of the cells C displayed on the display unit 74 is to be transferred (step S2). At this time point, there is no parameter (learning value) that defines the range of the cell C to be selected. Note that in step S2, the selection operation of the operator may be received after specifying the recommended cell C based on a setting value set in advance and displaying the recommended cell C on the display unit 74 in a visually recognizable manner.

Subsequently, the image processing unit 72 performs image processing of acquiring image data of the dish 2 supporting the cells C from the camera body 52, and specifying the cells C included in the image. The image processing data is sent to the analyzing unit 731 of the arithmetic unit 73. The analyzing unit 731 performs processing of determining the feature amount such as the shape, number, area, estimated volume, color, pattern, light intensity, and the like of the cell C selected by the operator and other cells C (step S3).

Then, with reference to the feature amount of the cell C selected by the operator among the feature amounts of respective cells C obtained by the analyzing unit 731, the specifying unit 732 determines the parameter that defines the range of the cell C to be selected. That is, the selection criterion of the cell C is learned (step S4). For example, when the area is selected as the feature amount, the parameter is a lower limit area threshold and an upper limit area threshold of the cell C preferable as the transfer target. When the color is selected as the feature amount, the parameter is lower limit average luminance threshold and upper limit average luminance threshold. Such a parameter is stored in a memory region (not shown) included in the control unit 7 (step S5).

Here, it is confirmed whether the operation mode has been changed by the mode changing unit 733 from the manual operation mode to the automatic approval mode (step S6). When the learning of the parameter is insufficient, the default manual operation mode is maintained (YES in step S6). Meanwhile, when the learning of the parameter is sufficiently advanced, for example, when the parameter stored in step S5 has reached a state where there is almost no variation in the latest plurality of updates, the operation mode is changed from the manual operation mode to the automatic approval mode (NO in step S6).

When the manual operation mode is maintained (YES in step S6), the image of the cell C supported on the dish 2 is again captured by the camera unit 5 (step S7/image capturing at the second time point). The image data obtained by this image capturing is subjected to the processing of specifying the cell C by the image processing unit 72 and the processing of extracting the feature amount of each cell C by the analyzing unit 731. Then, with reference to the current parameter (learning value), the specifying unit 732 specifies the recommended cell C on which the operator is prompted to make a selection among the cells C included in the captured image this time. Then, as shown in the procedure (D) of FIG. 3, the recommended cell C is displayed on the display unit 74 in a visually recognizable manner to the operator (step S8).

Subsequently, similarly to step S2, the input unit 75 receives input of the selection operation from the operator regarding which of the cells C displayed on the display unit 74 is to be transferred (step S9). Thereafter, the process returns to step S3, and the analyzing unit 731 specifies the feature amount of the cells C selected by the operator in step S9. Then, with reference to the feature amount of these cells C, the specifying unit 732 determines the parameter of the selection criterion of the cell C (step S4). At this time, if there is a discrepancy between the recommended cell C presented by the specifying unit 732 in the previous step S8 and the cell C actually selected by the operator in step S9, the parameter will be updated with a new value. In the image obtained by the next image capturing of the cell C (step S7/image capturing at the third time point), the recommended cell C is specified based on the updated parameter.

On the other hand, when the mode changing unit 733 changes the operation mode to the automatic approval mode (NO in step S6), the operator's selection operation is omitted thereafter. The image of the cells C supported on the dish 2 is captured by the camera unit 5 (step S10). Subsequently, the specifying unit 732 performs processing of specifying the recommended cell C among the cells C included in the obtained image (step S11). Then, the recommended cell C specified in step S11 is automatically selected as the transfer target cell C without receiving the operator's selection operation from the input unit 75 (step S12).

Thereafter, it is confirmed whether the image capturing of the cell C is continued (step S13). When the image capturing is continued (YES in step S13), returning to step S10, the camera unit 5 performs the next image capturing operation on the dish 2. On the other hand, when there is no cell C to be captured (NO in step S13), the process ends.

[Operational Effects]

With the image capturing system according to the present embodiment described above, in the selection operation on the cell C performed at the second time point or thereafter, the recommended cell C is presented to the operator on the display unit 74. This allows the operator to quickly select the cell C while referring to the recommended cell C. Moreover, the recommended cell C is highly accurate because the recommended cell C is specified based on the parameter which is based on selection records of the operator up to the first time point. Therefore, the operator can select the cell C accurately and can reduce the labor of the operator in the work of selecting the cell C.

If there is a discrepancy between the recommended cell C and the cell C actually selected by the operator at the second time point, the specifying unit 732 extracts the feature amount again (learns the feature amount), and the parameter serving as the selection criterion of the cell C is corrected based on the feature amount. Then, at the third time point, the recommended cell C is specified based on the corrected parameter. Therefore, in the selection operation at the third time point and thereafter, the accuracy of specifying the recommended cell C can be further improved. That is, in parallel with the operator's selection operation, the accuracy of specifying the recommended cell C can be gradually improved based on the learning effect of the feature amount.

Furthermore, the image capturing system of the present embodiment has a configuration in which the specifying unit 732 learns the feature amount based on the selection result of the operator. Therefore, when a plurality of operators are present, the specifying unit 732 can individually learn the feature amount according to the selection result of each operator. In this case, for example, when performing the selection operation from the input unit 75, the operation is received in association with the identification ID of the operator, and the learning data is generated for each operator and stored in a memory region of the arithmetic unit 73. This makes it possible to specify the individual recommended cell C based on selection tendency of each operator, rather than the average recommended cell C for all the operators.

Furthermore, the image capturing system of the present embodiment can cause the specifying unit 732 to learn the feature amount for each type or each individual of the biological subject, and cause the specifying unit 732 to specify the recommended cell C for each type or individual. For example, when different types of cancer cell such as, for example, a pancreatic cancer cell and an ovarian cancer cell are to be captured as the biological subject, a cancer cell classification determined in advance or the like is input before the selection operation of the cell C from the input unit 75 is performed. Then, the learning data is generated for each type of cancer cell according to the selection result of the operator, and is stored in a memory region of the arithmetic unit 73. This allows the specifying unit 732 to specify the recommended cell C according to the type of cancer cell.

Furthermore, for example, even for the same cancer cell, a test subject A and a test subject B different from each other may have different tendencies of cell necessary for experiments, tests, and the like. That is, the recommended cell C may differ depending on the individual even for the same cell type. The same applies when the recommended cell C is specified for each individual. In this case, before the selection operation of the cell C from the input unit 75 is performed, the identification ID and the like of the individual from whom the cell C is collected is input. Then, according to the selection result of the operator, the learning data is generated for each individual and stored in a memory region of the arithmetic unit 73. This allows the specifying unit 732 to specify the recommended cell C according to each individual.

In actual operations, if it is desired to specify the recommended cell C in units of individual and type, for example, if it is desired to specify the recommended cell C in units of "pancreatic cancer cell" of "test subject A", the ID or the like is input from the input unit 75 so that such individual and type classification can be performed. Meanwhile, if it is sufficient to perform classification by the unit of "pancreatic cancer cell", the ID related to the type or the like is input from the input unit 75. This makes it possible to generate the learning data in a required unit and to cause the specifying unit 732 to specify the recommended cell C suitable for the unit.

[Configurations Included in the Above Embodiment]

Note that the above-described specific embodiment mainly includes the following configurations.

An image capturing system according to one aspect of the present disclosure includes an image capturing device configured to simultaneously capture an image of a plurality of biological subjects; a display unit configured to display the image including the plurality of biological subjects captured by the image capturing device; an input unit configured to receive input from an operator regarding a selection operation on the plurality of biological subjects displayed on the display unit; an analyzing unit configured to analyze the image corresponding to each of the biological subjects to which the selection operation is given by the input unit and extract a feature amount about the biological subject; and an identifying unit configured to set a parameter that defines a range of each of the biological subjects to be selected based on the feature amount extracted by the analyzing unit for each of the biological subjects to which the selection operation is given by a first time point or a reference feature amount determined in advance, the identifying unit being configured to identify a recommended biological subject on which the operator is urged to make a selection based on the parameter in the image including the plurality of biological subjects obtained by image capturing at a second time point later than the first time point.

With this image capturing system, in the selection operation by the input unit performed at the second time point or thereafter, the recommended biological subject is presented to the operator. This allows the operator to quickly select the biological subject while referring to the recommended biological subject. Moreover, the recommended biological subject is highly accurate because the recommended biological subject is specified based on the parameter which is based on selection records of the operator up to the first time point or the reference feature amount. Therefore, the image capturing system can accurately select the biological subject and reduce the labor of work for selecting the biological subject.

In the image capturing system, preferably, when the input unit receives input of the selection operation of each of the biological subjects that does not agree with the recommended biological subject specified by the specifying unit in the selection operation on the plurality of biological subjects in the image obtained by the image capturing at the second time point, the analyzing unit analyzes the image corresponding to each of the biological subjects received by the input unit, and extracts the feature amount about the biological subject at the second time point, and the specifying unit corrects the parameter based on the feature amount at the second time point, and in the image including the plurality of biological subjects obtained by the image capturing at a third time point later than the second time point, the specifying unit specifies the recommended biological subject based on the corrected parameter.

With the image capturing system, at the second time point, if there is a discrepancy between the recommended biological subject and the selection record of the biological subject by the operator, the feature amount is extracted again (feature amount is learned), and the parameter is corrected based on the feature amount. Then, at the third time point, the recommended biological subject is specified based on the corrected parameter. Therefore, in the selection operation at the third time point and thereafter, the accuracy of specifying the recommended biological subject can be further improved. That is, in parallel with the operator's selection operation, the accuracy of specifying the recommended biological subject can be gradually improved based on the learning effect of the feature amount.

Preferably, the image capturing system further includes a mode changing unit configured to change an operation mode to treat the recommended biological subject specified by the specifying unit as the biological subject for which the selection operation is received by the input unit without receiving the selection operation.

With the image capturing system, the selection operation by the operator can be omitted when the mode changing unit changes the operation mode. It is assumed that, as the learning of the feature amount progresses, the accuracy of specifying the recommended biological subject increases to such an extent that intervention of the operator's selection operation is no longer required. At such timing, the work of selecting the biological subject can be completely automated by causing the mode changing unit to change the operation mode.

In the image capturing system, the feature amount may be a feature amount based on a shape of each of the biological subjects.

The image capturing system may further include a plate including a plurality of compartments configured to accommodate the biological subjects, wherein the image capturing device captures a state where the biological subjects are accommodated in the compartments of the plate, and the feature amount is a feature amount based on an amount of each of the biological subjects accommodated in one of the compartments. In this case, the amount of each of the biological subjects may be an amount obtained from at least one of a number, an area, and estimated volume estimated from a contour of the biological subject.

Alternatively, the feature amount may be a feature amount based on a color of each of the biological subjects, and the feature amount may be a feature amount based on a pattern of each of the biological subjects.

Furthermore, the feature amount may be a feature amount based on light intensity in a region of each of the biological subjects on the image. Alternatively, the feature amount may be a feature amount based on the light intensity of the region of each of the biological subjects and a peripheral region on the image.

Preferably, the image capturing system further includes: a plate including a plurality of compartments configured to accommodate the biological subjects; a head having a tip that picks up each of the biological subjects from each of the compartments of the plate, the head being capable of transferring the picked up biological subject; and a control unit configured to control an operation of the pickup by the tip, wherein the image capturing device captures an image of a state in which the biological subjects are accommodated in the compartments of the plate, and the control unit performs control to cause the tip to pick up each of the biological subjects to which the selection operation is given by the input unit or each of the biological subjects to which the selection operation is not given.

The image capturing system can have a function of picking up the biological subject to which the selection operation is given or is not given, and transferring the biological subject to a desired position.

In the image capturing system, when a plurality of operators are present, the specifying unit preferably specifies the recommended biological subject individually for each of the operators based on a learning result of the feature amount according to a selection result of each of the operators. This makes it possible to specify the individual recommended biological subject based on selection tendency of each operator, rather than the average recommended biological subject for all the operators.

In the image capturing system, when a plurality of types of biological subject exist, the specifying unit preferably specifies the recommended biological subject individually for each of the biological subjects based on a learning result of the feature amount according to a selection result of the operator on each of the biological subjects. This makes it possible to specify the recommended biological subject according to the type of biological subject, rather than the average recommended biological subject for all the biological subjects.

In the image capturing system, when an identical type of biological subject collected from a plurality of individuals exists, the specifying unit preferably specifies the recommended biological subject individually for each of the individuals based on a learning result of the feature amount according to a selection result of the operator on the biological subject of each of the individuals. This makes it possible to specify the recommended biological subject according to each individual, even for the identical type of biological subject.

The present disclosure described above can provide the image capturing system that can accurately select the biological subject and reduce the labor of work for selecting the biological subject.

What is claimed is:

1. An image capturing system comprising:
   an image capturing device configured to simultaneously capture an image of a plurality of biological subjects;
   a display configured to display the image including the plurality of biological subjects captured by the image capturing device;
   an input configured to receive input from an operator regarding a selection operation on the plurality of biological subjects displayed on the display;
   an analyzer configured to analyze the image corresponding to each of the biological subjects to which the selection operation is given by the input and extract a feature amount about the biological subject; and
   a specifying unit configured to set a parameter that defines a range of each of the biological subjects to be selected based on the feature amount extracted by the analyzer for each of the biological subjects to which the selection operation is given up to a first time point or a reference feature amount determined in advance, the specifying unit being configured to specify a recommended biological subject on which the operator is prompted to make a selection based on the parameter in the image including the plurality of biological subjects obtained by image capturing at a second time point later than the first time point, wherein
   when the input receives input of the selection operation of each of the biological subjects that does not agree with the recommended biological subject specified by the specifying unit in the selection operation on the plurality of biological subjects in the image obtained by the image capturing at the second time point,
   the analyzer analyzes the image corresponding to each of the biological subjects received by the input, and extracts the feature amount about the biological subject at the second time point, and
   the specifying unit corrects the parameter based on the feature amount at the second time point, and in the image including the plurality of biological subjects obtained by the image capturing at a third time point later than the second time point, the specifying unit specifies the recommended biological subject based on the corrected parameter.

2. The image capturing system according to claim 1, further comprising a mode changing unit configured to change an operation mode to treat the recommended biological subject specified by the specifying unit as the biological subject for which the selection operation is received by the input without receiving the selection operation.

3. The image capturing system according to claim 2, further comprising:
   a plate including a plurality of compartments configured to accommodate the biological subjects;
   a head having a tip configured to pick up each of the biological subjects from each of the compartments of the plate, the head being configured to transfer the picked up biological subject; and
   a controller configured to control an operation of the pickup by the tip,
   wherein the image capturing device captures an image of a state in which the biological subjects are accommodated in the compartments of the plate, and the controller is configured to cause the tip to pick up each of the biological subjects to which the selection operation is given by the input unit or each of the biological subjects to which the selection operation is not given.

4. The image capturing system according to claim 1, wherein the feature amount is a feature amount based on a shape of each of the biological subjects.

5. The image capturing system according to claim 1, wherein the feature amount is a feature amount based on a color of each of the biological subjects.

6. The image capturing system according to claim 1, wherein the feature amount is a feature amount based on a pattern of each of the biological subjects.

7. The image capturing system according to claim 1, wherein the feature amount is a feature amount based on light intensity in a region of each of the biological subjects on the still image.

8. The image capturing system according to claim 7, wherein the feature amount is a feature amount based on the light intensity of the region of each of the biological subjects and a peripheral region on the still image.

9. The image capturing system according to claim 1, further comprising:
   a plate including a plurality of compartments configured to accommodate the biological subjects;
   a head having a tip configured to pick up each of the biological subjects from each of the compartments of the plate, the head being configured to transfer the picked up biological subject; and
   a controller configured to control an operation of the pickup by the tip,
   wherein the image capturing device captures an image of a state in which the biological subjects are accommodated in the compartments of the plate, and
   the controller is configured to cause the tip to pick up each of the biological subjects to which the selection operation is given by the input unit or each of the biological subjects to which the selection operation is not given.

10. The image capturing system according to claim 1, wherein the feature amount is a feature amount based on a shape of each of the biological subjects.

11. The image capturing system according to claim 1, further comprising a plate including a plurality of compartments configured to accommodate the biological subjects,
   wherein the image capturing device captures a state where the biological subjects are accommodated in the compartments of the plate, and
   the feature amount is a feature amount based on an amount of each of the biological subjects accommodated in one of the compartments.

12. The image capturing system according to claim 1, wherein the feature amount is a feature amount based on a color of each of the biological subjects.

13. The image capturing system according to claim 1, wherein the feature amount is a feature amount based on a pattern of each of the biological subjects.

14. The image capturing system according to claim 1,
   An image capturing system comprising:
   an image capturing device configured to simultaneously capture a still image of a plurality of biological subjects;
   a display configured to display the still image including the plurality of biological subjects captured by the image capturing device;
   an input configured to receive input from an operator regarding a selection operation on the plurality of biological subjects displayed on the display;
   an analyzer configured to analyze the still image corresponding to each of the biological subjects to which the selection operation is given by the input and extract a feature amount about the biological subject;
   a specifying unit configured to set a parameter that defines a range of each of the biological subjects to be selected based on the feature amount extracted by the analyzer for each of the biological subjects to which the selection operation is given up to a first time point or a reference feature amount determined in advance, the specifying unit being configured to specify a recommended biological subject on which the operator is prompted to make a selection based on the parameter in the still image including the plurality of biological subjects obtained by image capturing at a second time point later than the first time point; and
   a plate including a plurality of compartments configured to accommodate the biological subjects,
   wherein the image capturing device captures a state where the biological subjects are accommodated in the compartments of the plate, and
   the feature amount is a feature amount based on an amount of each of the biological subjects accommodated in one of the compartments.

15. The image capturing system according to claim 14, wherein the amount of each of the biological subjects is an amount obtained from at least one of a number, an area, and estimated volume estimated from a contour of the biological subject.

16. An image capturing system comprising:
   an image capturing device configured to simultaneously capture an image of a plurality of biological subjects;
   a display configured to display the image including the plurality of biological subjects captured by the image capturing device;
   an input configured to receive input from an operator regarding a selection operation on the plurality of biological subjects displayed on the display;
   an analyzer configured to analyze the image corresponding to each of the biological subjects to which the selection operation is given by the input and extract a feature amount about the biological subject; and
   a specifying unit configured to set a parameter that defines a range of each of the biological subjects to be selected based on the feature amount extracted by the analyzer for each of the biological subjects to which the selection operation is given up to a first time point or a reference feature amount determined in advance, the specifying unit being configured to specify a recommended biological subject on which the operator is prompted to make a selection based on the parameter in the image including the plurality of biological subjects obtained by image capturing at a second time point later than the first time point, further comprising:
   a plate including a plurality of compartments configured to accommodate the biological subjects;
   a head having a tip configured to pick up each of the biological subjects from each of the compartments of the plate, the head being configured to transfer the picked up biological subject; and
   a controller configured to control an operation of the pickup by the tip,
   wherein the image capturing device captures an image of a state in which the biological subjects are accommodated in the compartments of the plate, and
   the controller is configured to cause the tip to pick up each of the biological subjects to which the selection operation is given by the input or each of the biological subjects to which the selection operation is not given.

17. The image capturing system according to claim 16, wherein when a plurality of operators are present, the specifying unit specifies the recommended biological subject individually for each of the operators based on a learning result of the feature amount according to a selection result of each of the operators.

18. The image capturing system according to claim 16, wherein when a plurality of types of biological subject exist, the specifying unit specifies the recommended biological subject individually for each of the biological subjects based on a learning result of the feature amount according to a selection result of the operator on each of the biological subjects.

19. The image capturing system according to claim 16, wherein when an identical type of biological subject collected from a plurality of individuals exists, the specifying unit specifies the recommended biological subject individually for each of the individuals based on a learning result of the feature amount according to a selection result of the operator on the biological subject of each of the individuals.

* * * * *